(12) United States Patent
Staege et al.

(10) Patent No.: US 6,194,205 B1
(45) Date of Patent: Feb. 27, 2001

(54) METHOD FOR THE STIMULATION OF T CELLS HAVING A DESIRED ANTIGEN SPECIFICITY

(75) Inventors: Martin Staege; Bettina Kempkes; Georg W. Bornkamm; Wolfgang Hammerschmidt, all of Munich; Ursula Zimber-Strobl, Germering; Axel Polack, Munich, all of (DE)

(73) Assignee: GSF-Forschungszentrum fur Umwelt und Gesundheit GmbH, Neuherberg (DE)

(*) Notice: Subject to any disclaimer, the term of this patent is extended or adjusted under 35 U.S.C. 154(b) by 0 days.

(21) Appl. No.: 09/152,653

(22) Filed: Sep. 14, 1998

(30) Foreign Application Priority Data

Sep. 15, 1997 (DE) .............................. 197 40 571

(51) Int. Cl.$^7$ ....................................... C12N 5/10
(52) U.S. Cl. .................... 435/373; 435/467; 435/375; 435/372.3
(58) Field of Search ................. 435/69.1, 69.52, 435/69.7, 455, 325, 355, 362, 366, 372, 372.7, 373, 375, 320.1, 467; 424/85.2, 93.1, 93.21, 93.71

(56) References Cited

U.S. PATENT DOCUMENTS 5,629,159 * 5/1997 Anderson .................................. 435/6

FOREIGN PATENT DOCUMENTS

WO 96/00285  1/1996 (WO).
WO 96/07733  3/1996 (WO).

OTHER PUBLICATIONS

Kempkes, B. et al., Epstein–Barr virus nuclear antigen 2 . . . , Journal of General Virology 77, p227–237, Feb. 1996.*

* cited by examiner

*Primary Examiner*—David Guzo
*Assistant Examiner*—Gerald G. Leffers, Jr.
(74) *Attorney, Agent, or Firm*—Townsend and Townsend and Crew LLP

(57) ABSTRACT

T cells having a desired antigen specificity are stimulated by (a) introducing immortalizing genes into antigen-presenting cells in a manner permitting regulation of the expression and/or function of at least one of these genes to achieve conditionally immortalized antigen-presenting cells; (b) introducing a gene encoding the desired antigen into the immortalized cells in a manner permitting the antigen to be expressed after the expression and/or abolishment of the function of at least one of the immortalizing genes stops; (c) expanding the immortalized antigen-presenting cells by expression and/or functional activation of the immortalizing genes; (d) completing the proliferation of the immortalized antigen-presenting cells by stopping the expression and/or abolishing the function of at least one of the controllable immortalizing genes; (e) continuing the expression of the antigen; (f) adding leucocytic cells including T cells and cultivating the cell mixture to stimulate the T cells directed against the desired antigen; and (g) optionally purifying and isolating the stimulated T cells.

22 Claims, 3 Drawing Sheets

METHOD FOR THE STIMULATION OF T CELLS HAVING A DESIRED ANTIGEN SPECIFICITY

BACKGROUND OF THE INVENTION

1. Field of the Invention

The present invention relates to methods for the stimulation of T cells having a desired antigen specificity.

2. Description of the Prior Art

The different sub-populations of T cells play an important role on the one hand in the regulation of immunological processes and on the other hand as the effector cells of cytotoxicity in the defense of infectious diseases and malignant growth of new tumors as well as in the development of autoimmune diseases. Therefore, a modulation of T cell activity is of central interest in the context of the treatment of numerous diseases. According to the invention, "stimulation" refers not only to an enhancement of a preexisting T cell-mediated immune response but also to its induction to achieve a defense against pathogens or tumor cells; furthermore, in the case of autoimmune diseases and allergies it is desired to suppress the undesired immune response.

In the past it has been tried in several ways to induce a T cell reaction. On the one hand, the native antigen [2] or antigenic peptides [3, 4] have been employed in vivo and in vitro to induce a T cell response, on the other hand the gene encoding the respective antigen has been introduced in suitable cells by means of gene tranfer and the cells thus modified have been employed as antigen-presenting cells (APCs). Because of their superior immunostimulatory properties, particularly dendritic cells (DCs) have been used for this purpose [5].

These methods bear several advantages and disadvantages. Thus, the use of native antigens is not suitable for an induction of cytotoxic T cells (CTLs). CTLs recognize the relevant antigenic peptide i.e. in combination with class I molecules of the major histocompatibility complex (MHC). However, generally the peptides presented in combination with class I MHC molecules are derived from intracytoplasmic antigen processing. Since exogenously added antigens do not enter the class I way of antigen processing it is generally impossible to induce CTLs by immunization with native antigens.

Peptides, in contrast, have the advantage of being able to externally bind to MHC molecules without having to enter the cytoplasm of APCs. However, a prerequisite for the use of peptides for T cell generation or T cell stimulation, respectively, is that the antigenic determinants (epitopes) of the individual antigens must be known. Since MHC molecules can only bind to peptides having conserved structural features but since these consensus sequences are determined by the MHC molecule and are different for each allele, it would be necessary to re-determine the suitable peptides for each MHC haplotype/antigen combination. This not only takes up a great deal of time and effort but, in addition, the technology required is not always available. Moreover, at least the use of peptides in vivo is questionable because in addition to induction of a specific T cell immunity it may also cause an induction of a specific tolerance [6].

The use of antigen-presenting DCs in the immunization is limited by difficulties in isolation, culture and gene transfer into these cells and, furthermore, by strong limitations in the number of DCs available for many diseases.

Besides DCs, the activated B cells are the most potent APCs known. Interestingly, the immortalization of B cells with Epstein-Barr virus results in cells (lymphoblastoid cell lines, LCL) representing the phenotype of activated B cells [7]. These cells are excellent APCs, have a nearly unlimited potential to proliferate and, thus, are also used as such for numerous immunological experiments in the human system for which a regular access to other APCs is not necessary and/or not justified for ethical reasons. Basically, LCLs should be suited as APCs for the induction of any desired T cell response. However, this is impeded by the fact that such cells also induce a strong EBV-specific T cell-mediated immune response interfering with the desired immune reaction [8, 9, 10]. Since the frequency of EBV in the population is extremely high and the frequency of EBV-specific T cells in persons with latent EBV infection is one of the highest T cell frequencies known (only comparable to the frequency of allospecific T cells) EBV-immortalized autologous B cells are well suited for re-stimulation but are unsuitable for a primary stimulation of T cells which do not recognize EBV antigens.

SUMMARY OF THE INVENTION

It is an object of the present invention to provide a novel method for the stimulation of T cells having a desired antigen specificity.

According to the invention, this object has been solved by a method (1) comprising at least the following steps:

(a) introducing immortalizing genes into antigen-presenting cells (APCs) in a way that at least the expression and/or function of at least one of these genes may be regulated to achieve conditionally immortalized antigen-presenting cells;

(b) introducing a gene encoding the desired antigen into the immortalized cells obtained in step (a) in a way that the antigen may also be expressed at least after stop of the expression and/or abolishment of the function of at least one of the immortalizing genes;

(c) expanding the immortalized antigen-presenting cells by expression of the immortalizing genes and/or by functional activation of the immortalizing genes;

(d) completing the proliferation of the immortalized antigen-presenting cells by stopping the expression and/or abolishing the function of at least one of the controllable immortalizing genes;

(e) continued expression of the antigen;

(f) adding leucocytic cells at least including T cells and cultivating the cell mixture to stimulate the T cells directed against the desired antigen;

(g) optionally purifying and isolating the stimulated T cells.

DESCRIPTION OF THE PREFERRED EMBODIMENTS

Figure 1:
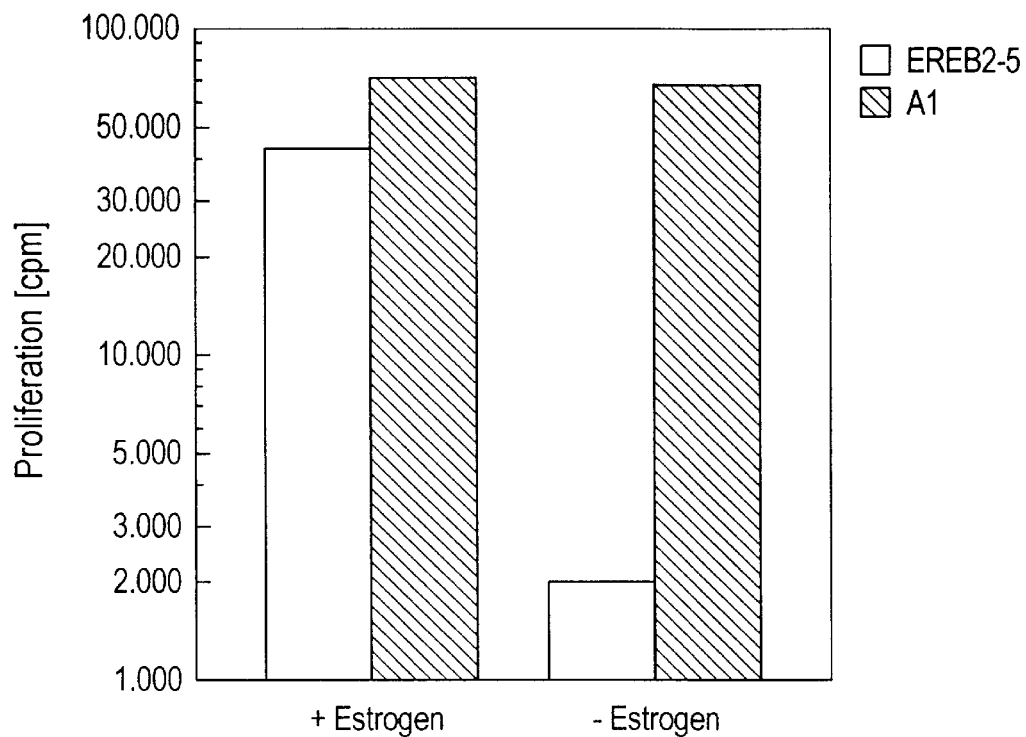
FIG. 1 shows that A1 cells but not EREB2–5 cells continue to proliferate after estrogen depletion.

In one embodiment of this method in step (a) there are added APCs derived from a donor A and in step (f) there are added allogenic leucocytic cells from another donor B who is syngenic with APC donor A in at least one corresponding MHC molecule serving for antigen presentation.

In a further embodiment the antigen-presenting cells used in step (a) may be derived from the same donor as are the leucocytic cells of step (f).

It is not absolutely necessary to perform the above-described steps in the sequence listed. It is also possible to vary the sequence of these steps still leading to the desired stimulation of T cells with the desired antigen specificity. For example, step (b) may be carried out directly prior to step (e) without departing from the invention.

In the following, a further embodiment of the method of the invention will be described comprising the following steps and also leading to the desired stimulation of T cells having the desired antigen specificity:

(a) introducing immortalizing genes into antigen-presenting cells (APCs) in a way that at least the expression and/or function of at least one of these genes may be regulated to achieve conditionally immortalized antigen-presenting cells;

(b) introducing a gene encoding the desired antigen into the immortalized cells obtained in step (a) in a way that the antigen may also be expressed at least after stop of the expression and/or abolishment of the function of at least one of the immortalizing genes;

(c) expanding the immortalized antigen-presenting cells by expression of the immortalizing genes and/or by functional activation of the immortalizing genes;

(d) adding leucocytic cells at least including T cells to a first portion (aliquot) of the immortalized cells obtained in steps (a) to (c) expressing the desired antigen and culturing the cell mixture to stimulate the T cells directed against the desired antigen;

(e) completing the proliferation of the second portion of the APCs obtained in steps (a) to (c) by stopping the expression and/or abolishing the function of at least one of the controllable genes required for immortalization;

(f) co-cultivating the antigen-presenting cells after stop of the expression and/or abolishment of the function of at least one of the controllable immortalizing genes of (e) with the T cells stimulated in step (d) for re-stimulation of the T cells directed against the desired antigen; and (g) optionally purifying and isolating the stimulated T cells.

This latter method described is referred to a method No. 2. The method No. 2 may be developed as follows:

In step (a) there are added APCs derived from a donor A and in step (d) there are added allogenic leucocytic cells from another donor B who is syngenic with the donor A of the APCs for at least one corresponding MHC molecule serving for antigen presentation.

In a preferred embodiment of the invention, the APCs used in step (a) of the method No. 2 are derived from the same donor as are the leucocytic cells in step (d).

As already described for the method No. 1, it is also not absolutely necessary in the performing of method No. 2 to carry out the process steps (a) to (g) in the sequence indicated, but the skilled artisan will recognize modifications which also lead to the desired stimulation of antigen-specific T cells. For example, step (b) may be carried out immediately prior to step (d) or step (b) may be carried out immediately prior to steps (d) and (f).

As detailed above the term "stimulation" used in the Claims comprises not only an induction of a T cell-mediated immune response but also an enhancement of a pre-existing T cell-mediated immune reaction or the induction of an anergy in the stimulated T cells.

According to the invention, antigen-presenting cells, in the following abbreviated as "APCs", are conditionally immortalized to be able to regulate at least the expression and/or the function of one of the genes required for immortalization. As APCs there may be employed any antigen-presenting cells known to the skilled artisan capable of presenting the antigen in a way that it may be recognized by T cells. Preferably, B cells, macrophages, dendritic cells and/or fibroblast cells may be employed as antigen-presenting cells with B cells being particularly preferred.

"Immortalizing genes" according to the invention refers to such genes required to immortalize the antigen-presenting cells, i.e. the functional expression of which in suitable cells either alone or in combination with other factors leads to an unlimited proliferation of these cells. Preferably, B cells are used which have been immortalized so that their antigen-presenting properties are combined with the ability of unlimited expansion of those cells in culture. Thus, the immortalized antigen-presenting cells which may be derived from any donor are available in an unlimited amount for the primary and secondary stimulations of T cells.

The genes required for immortalization are for example derived from the Epstein-Barr virus (EBV) or from adenoviruses; however, also oncogenes may be used for immortalization. The genes which are in each case at least required for immortalization of the APCs are either reported in the literature or may be obtained by deletions starting from the entire genome. For example, the immortalizing genes of EBV are present on mini-EBV vectors which are e.g. described in [11]. For completeness of the disclosure, this reference is incorporated by reference in its entirety.

It is particularly preferred to select the genes among the immortalizing genes of EBV, for example EBNA2, EBNA3a, EBNA3b, EBNA3c, or LMP genes.

Besides EBV, for example adenoviruses may be used to generate conditionally immortalized APCs. Spitkovsky et al. (J. Virol. 1994, 68(4):2206) have demonstrated that it is possible to conditionally immortalize cells with the adenoviral E1A gene if this gene has been fused to the hormone-binding domain of the estrogen receptor and the c-ras gene is simultaneously expressed in the cells. While the authors used fibroblasts as the target cells, it has been already shown years ago that fibroblasts may serve quite reasonably as APCs if they are transfected with CD54 and MHC molecules. Thus, it might be possible to transfect fibroblasts with vectors containing E1A conditionally as well as e.g. CD54, HLA-A2.1, and cdk-$4^{R23C}$ (a tumor antigen presented in combination with HLA-A2 and in this case representing the desired antigen), to expand those cells in the presence of the EA function, and then, after the E1A function has been switched off to employ those cells as APCs for the respective leucocytic cells.

To immortalize the antigen-presenting cells also transforming genes such as oncogenes may be employed. For example the concomitant overexpression of c-myc and another oncogene such as ras or abl results in a transformation of cells. For example one of the oncogenes such as the c-myc oncogene may be rendered controllable by an antibiotic such as tetracycline so that the conditionally immortalized antigen-presenting cells proliferate only in the absence of the antibiotic, i.e. in the presence of myc expression.

According to the invention at least one of the genes required for immortalization, e.g. of EBV, is present in a controllable form. "Regulation" means that the expression of this gene or the function of this gene is controllable in a way that by switching on or off the gene or the function of its protein the proliferation of the antigen-presenting cells may be stopped.

Besides the possibility to render the expression of a gene required for immortalization controllable it is possible to express the respective gene in a constitutive manner but in a form in which the function of the protein generated may be regulated e.g. by hormones. Constitutive expression of a fusion protein of the hormone binding site of the estrogen receptor and the desired immortalizing agent may for example lead to the translocation into the nucleus only after estrogen is bound to the receptor portion of the fusion protein where the function of the immortalizing portion of the fusion protein will become active.

As the controllable EBV gene required for immortalization there may be for example used: the EBNA2 gene, the EBNA3a gene, the EBNA3b gene, the EBNA3c gene, or the LMP gene.

The regulation of the controllable immortalizing gene may be carried out using any method known from the prior art. For example, a hormone binding site may be cloned into the upstream region of the transcriptional unit encoding the gene to render the gene product functional in the presence of hormone and non-functional in the absence of hormone. Besides hormones, there may be also used binding sites for antibiotics. As the hormone-binding site there may be for example used an androgen or estrogen binding site.

In a preferred embodiment the gene coding for the desired antigen is present on the same vector which also bears the genes required for immortalization at least one of which, as detailed above, must be present in a controllable form.

Introduction of the EBV genes required for immortalization and introduction of a gene encoding the desired antigen may be performed either separately or in one step, the genes required for immortalization and the gene encoding the desired antigen being preferably arranged on one vector.

As the vectors for introduction of the gene coding for the desired antigen, there may be used any vectors known from the prior art and useful for the expression of the desired antigen in the immortalized antigen-presenting cell. In the following, the present invention will be described referring to an Example of an antigen which has been introduced into the cell by means of a vaccinia-derived vector. However, also other vectors may be used, for example those derived from EBV, adenoviruses, from retroviruses, from foamy viruses, poxviruses different from vaccinia, or from SV40.

Any antigen may be cloned into the vectors and may be introduced into the APCs using these vectors. Possible antigens listed herein only by means of example are: viral antigens, for example that of pp65 of the human cytomegalo-virus, or the EBNA3b of EBV; tumor antigens, such as the $p16^{INK4a}$-insensitive mutant of cdk4 or the bcr-abl fusion protein; bacterial antigens, such as listeriolysin or streptolysin, or model antigens employed in experimentation such as ovalbumin or chicken egg-white lysozyme.

Expansion of the immortalized APCs is carried out under conditions known per se adjusted according to the antigen-presenting cell used.

After introduction of the gene encoding the desired antigen and the EBV genes required for immortalization into the antigen-presenting cells, those cells are expanded until a sufficiently high cell number is obtained. By stopping the expression of at least one of the controllable genes required for immortalization or by abolishing its function the proliferation and, thereby, the expansion of the antigen-presenting immortalized cells is stopped. However, the expression of the antigen is continued since it is not affected by the proliferation stop.

After completion of proliferation of the immortalized antigen-presenting cells, leucocytic cells at least including T cells are added, and this cell mixture is cultured to stimulate T cells directed against the desired antigen.

Leucocytic cells in the sense of this work are cells which may be enriched for example from the peripheral blood of a donor, e.g. by density gradient centrifugation, particularly preferred at a densitiy of 1.077 adjusted for example with Ficoll. Besides monocytes and NK cells these preparations contain mainly lymphocytes and predominantly T cells. These also include peripheral blood mononucleated cells (PBMC) at least including T cells.

Culturing of said cells together with the antigen-presenting cells is effected under culture conditions known per se. Preferred culture conditions are in Iscov's modified Dulbecco's medium (IMDM) or in RPMI1640 with the usual additions such as antibiotics, interleukin-2 and serum depending on the medium used. The cultivation is performed for a period required to achieve the desired object, generally for 7 to 40 days. The induced T cells may be purified and isolated by methods known per se. An example is the use of antibodies coupled to magnetic beads.

After starting the culture, the experimentalist experienced in the cultivation of T cells will adjust at least during the first week of cultivation by daily control the optimal culture conditions (IL-2 concentration, serum concentration, frequency of re-stimulation). Media which may be used include for example the following: RPMI+10% FCS+10 U/ml of IL-1 (Boehringer, Mannheim)+pen/strep+amphotericin B as well as CG medium (Vitromex, IMDM-based medium) with 10 U/ml of IL-2, 5% FCS+pen/strep+amphotericin B. Usually the cultivation is carried out for 7 days before the result of the experiment is determined or re-stimulation with fresh antigen is carried out.

By the method of the invention, antigen-specific cytotoxic T cells and/or T helper cells and/or T cells having suppressor properties are induced for example class I MHC-restricted cytotoxic T cells and class II MHC-restricted T helper cells, respectively. Thus, there may be induced antigen-specific CD8-positive and/or CD4-positive T cells having $\alpha\beta$ T cell receptors and/or $\gamma\delta$ T cell receptors.

It has to be noted that that it is not absolutely required to perform the introduction of the antigen prior to the expansion of the APCs but that it may be also carried out immediately prior to incubation with the leucocytic cells for example if vaccinia vectors are employed.

"Leucocytic cells" also includes peripheral blood mononucleated cells (PBMC) at least including T cells.

Preferably, prior to addition of leucocytic cells the immunostimulatory properties of the immortalized cells expressing the desired antigen are modulated. Modulation means that the property of the antigen-presenting cells to cause activation of T cells is altered in the desired manner. It is not absolutely necessary that this leads to an improvement of the stimulatory properties as it may be achieved in the case of B cells (as a basis for the conditionally immortalized APCs) e.g. by cultivation in the presence of a CD40 stimulus. In contrast, this modulation may for example alter the immunostimulatory properties in a way that an anergy is induced in the T cells. For this purpose, a treatment of the conditionally immortalized APCs with antibodies having a specificity for the B7½ co-stimulatory molecule would be useful.

Prior to co-cultivation of the conditionally immortalized antigen-presenting cells with the leucocytic cells for the stimulation of the T cells included, the immortalized APCs may be for example modulated by cultivation in the presence of a CD40 stimulus or in the presence of cytokines.

The CD40 stimulus may be obtained by addition of feeder cells expressing CD40 and co-cultivation of the immortalized antigen-presenting cells and the feeder cells, or the CD40 stimulus may be achieved by adding a soluble CD40 ligand or an anti-CD40 antibody.

The CD40 ligand-expressing feeder cells used herein have been described in: Galibert L., Burdin N., des Saint-Vis B., Garrone P., Van Kooten C., Banchereau J. and Rousset F. (1996). CD40 and B cell antigen receptor dual triggering of resting B lymphocytes turns on a partial germinal center phenotype, J.Exp.Med. 183:77.

Following inactivation (either by stopping the expression or blocking the function) of the gene required for immortalization, the conditionally immortalized antigen-presenting cells have only a short life period. This may be substantially prolonged by cultivation on a feeder layer expressing a CD40 ligand (CD40L) [13]. Remarkably, by the treatment with CD40L-expressing feeder cells also the stimulatory capacity of these cells for allogenic PBMC was preserved. The CD40L-expressing feeder cells are co-cultured with the immortalized antigen-presenting cells. However, it is also possible to perform the CD40 stimulus by adding a soluble CD40 ligand or an anti-CD40 antibody.

In a preferred embodiment of the invention, growth of the immortalized APCs is permanently suppressed prior to the addition of leucocytic cells. This permanent suppression may be effected for example by addition of mitomycin C or irradiation.

In the following the invention will first be again described in summary referring to the accompanying Figures. The Figures show:

An essential factor for immortalization by EBV is the EBV nuclear antigen 2 (EBNA2). There are also known B cells conditionally immortalized by EBV referred to as LCLs. This may be for example achieved by complementation of the EBNA2 deletion of the P3HR1 virus with a fusion protein consisting of EBNA2 and the hormone-binding domain of the estrogen receptor. Such constructions are known and have been described for example in [11]. These cells named EREB2–5 proliferate in the presence of estrogen. In the absence of estrogen EBNA2 is inactive and the cells cease to proliferate. It is also known that by transfection of EREB2–5 cells with an activated c-myc gene an EREB2–5 cell line (A1) may be established which grows also in the absence of estrogen [12]. These cells show many of the properties such as the growth, expression of surface antigens etc. of Burkitt's lymphoma cells, i.e. of cells in which EBV persists in the form of the so-called latency I.

In the experiments conducted according to the invention the immune reaction induced by the conditionally immortalized lymphoblastoid cell line (LCL) EREB2–5 and the c-myc-transfected daughter cell line A1 was characterized first. The EREB2–5 cells cultured in the presence of estrogen were found to induce a strong immune response of allogenic peripheral blood mononucleated cells (PBMCs) while A1 cells cultured in the absence of estrogen are unable to induce this response. Similarly A1 cells are not lysed by EBV-specific CTLs under these conditions while EREB2–5 cells are. We raised the question whether by modulating EBNA2 function in EREB2–5 cells or A1 cells, respectively, it will be possible to control the recognizability of these cells for the immune system.

By restoring EBNA2 function in A1 cells by cultivation in the presence of estrogen these cells regained their immunostimulatory capacity. In contrast, EREB2–5 cells surprisingly nearly completely lost their allostimulatory competence after 4 days of cultivation in the absence of estrogen. Lysis of EREB2–5 cells by CTLs having a specificity for the EBNA2-regulated EBV antigen LMP2 also was no longer detectable after estrogen depletion. However, EREB2–5 cells were in contrast lysed by CTLs also in the absence of estrogen if the respective antigen was expressed by infecting the cells with recombinant vaccinia viruses or the MHC molecules were exogenously charged with the relevant peptides. In this case lysis of the cells was only slightly reduced.

We used B cells as the APCs since the culture of APCs derived from B cells (tumor cell lines or LCLs) could be most conveniently performed. Blood from the umbilical cord of a healthy child from which the leucocytic cells, in this case PBMCs, were obtained served as the source for these B cells. The HLA haplotype of the donor of the PBMCs was (A11,28; B7,49; Cw7; DRw6,7; DQw1,2). As the immortalizing genes we used the respective EBV genes; the B cells were co-infected by the P3HR1 virus and a mini-EBV expressing the EBNA2 gene fused to the estrogen receptor. These vectors are described in Kempkes et al. (EMBO J. 14:88). This procedure led to the introduction of all of the EBV immortalizing genes into the cells by the P3HR1 virus (a type II EBV) with the exception of the EBNA2 gene which has been deleted in this virus strain. This gene could be functionally regulated by its fusion to the estrogen receptor: Only in the presence of estrogen in the culture medium the EBNA2 function is active. Therefore, these conditionally immortalized LCLs proliferate only in the presence of estrogen. Since the expression of essential EBV genes is controlled by EBNA2 also the expression of other EBV genes is down-regulated in these LCLs after the EBNA2 function has been switched off. These cells have been named EREB2–5 (for Estrogen Receptor/EBNA2 clone 5) and expanded in the presence of estrogen. In FIG. 1 the proliferation as a measured parameter for the expansion is shown. This Figure also demonstrates that the proliferation ceases after estrogen depletion, i.e. inactivation of the controllable immortalizing gene.

As antigens we have particularly used the EBNA3b gene of EBV type 1. Since the sequences of the EBNA3b genes of EBV type II used for immortalization (P3HR1) and type I strongly differ from each other, this antigen is one being expressed only after it has been artificially introduced into the cells. As the vector for introduction of the antigen recombinant vaccinia viruses have been used. These vectors have been described in "N. M. Steven, A. M. Leese, N. E. Annels, S. P. Lee, and A. Rickinso, 1996, Epitope focussing in the primary cytotoxic T cell response to Epstein-Barr Virus and is in relationship to T cell memory, J. Exp. Med. 184:1801).

Figure 2:
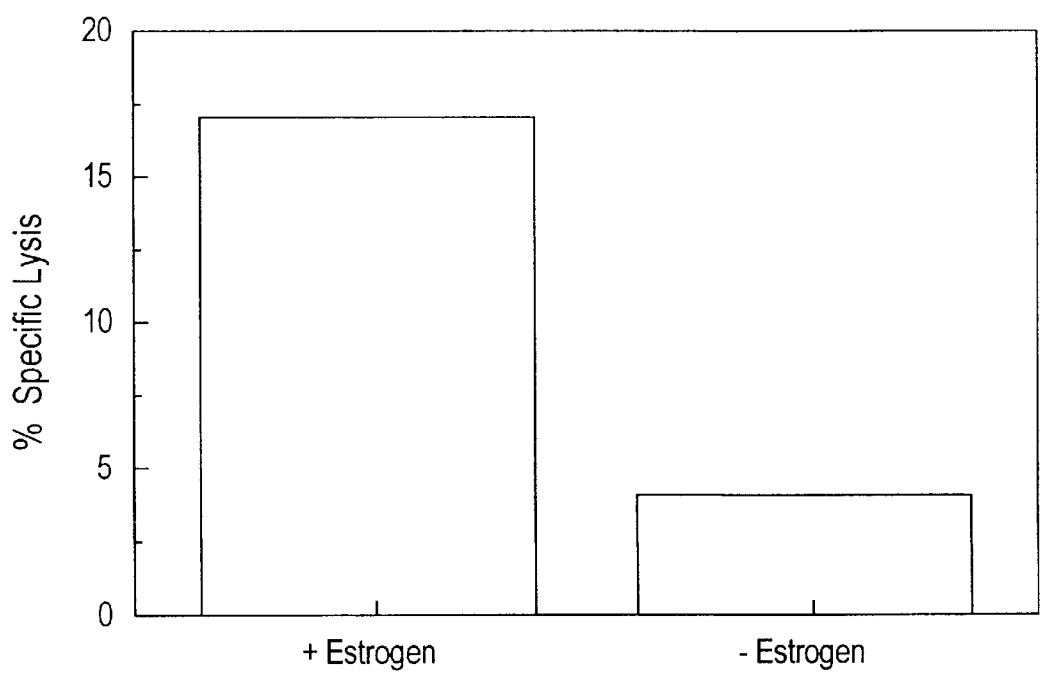
FIG. 2 shows that EREB2–5 cells are lysed by EBV-specific CTLs only in the presence of functional EBNA2.
Figure 4:
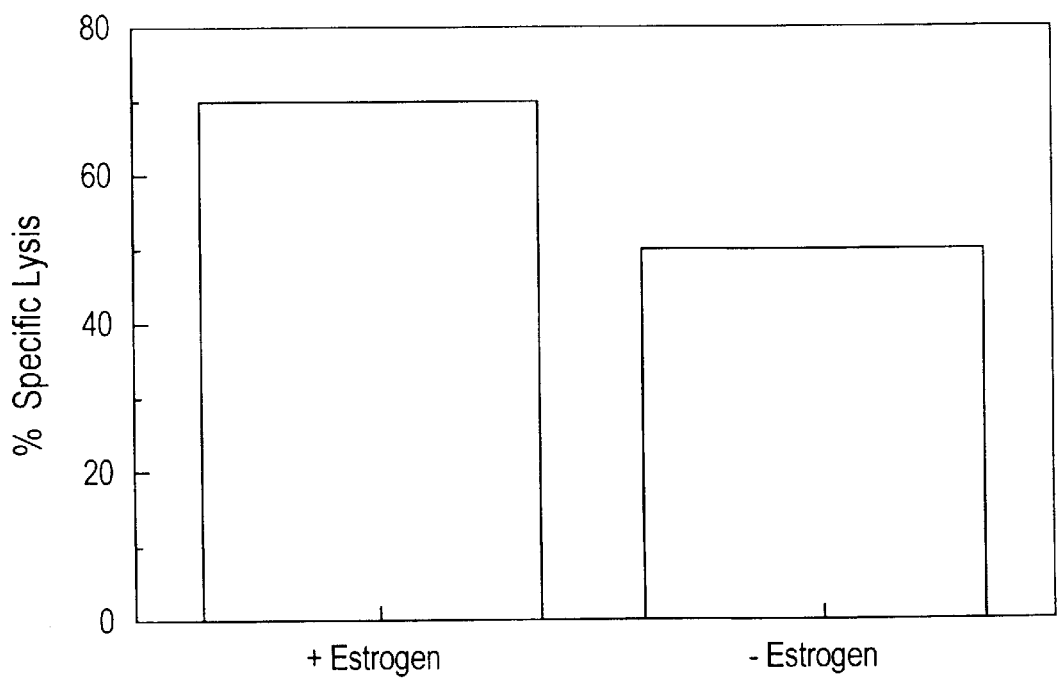
FIG. 4 shows that lysis of EREB2–5 cells by antigen-specific CTLs takes place also in the absence of estrogen if the relevant antigen is subjected to constitutive expression.

After introduction of EBNA3b by means of vaccinia virus, EREB2–5 cells were found to be successfully lysed by CTLs having a specificity for this antigen. This lysis took place also after the EBNA2 function had been switched off by estrogen depletion (FIG. 4). The CTLs used were syngenic in the HLA A11 allele with the EREB2–5 employed as the target cells but were derived from unrelated donors so that they may be referred to as (semi-) allogenic T cells. The T cells used are T cells which were established earlier by co-cultivation with EBV-positive cells from the T cell donors. Thus, this is an example for a re-stimulation of the T cells with allogenic LCLs syngenic in a HLA molecule serving for antigen presentation (in this case HLA A11). Obviously, CTLs may be well stimulated by the LCLs used; however, by modifications described above also T helper cells may be principally stimulated without any problems. That LCLs in principle have this potential may be demonstrated by the fact that if EREB2–5 cells are used for the stimulation of alloreactive cells CD8-positives (CTLs) and also CD4-positives (T helper cells) may be detected by immunofluorescence in the stimulated cells. (Data not shown; the FACS (fluorescence-activated cell scanner) analysis performed for this purpose has been carried out by methods similar to those described in reference 15). Lysis of EREB2–5 cells by CTLs having a specificity for an antigen being expressed under the control of EBNA2 (LMP2) occurred only in the presence of EBNA2 function (FIG. 2). Thus, it could be demonstrated that after switching off the EBNA2 function and, thereby, abolishing the immortalization the immune response against the immortalizing agent was strongly reduced what in the end is the most important advantage of the use of conditionally immortalized cells over the classical immortalized APCs for the use as APCs in T cell stimulation.

The further experiments were conducted using as the APCs EREB2–5 cells without further introduction of an antigen as stimulatory cells for allogenic PBMCs. In this case, the ubiquitous alloantigens (mainly the allogenic HLA) served as the antigen.

Figure 3:
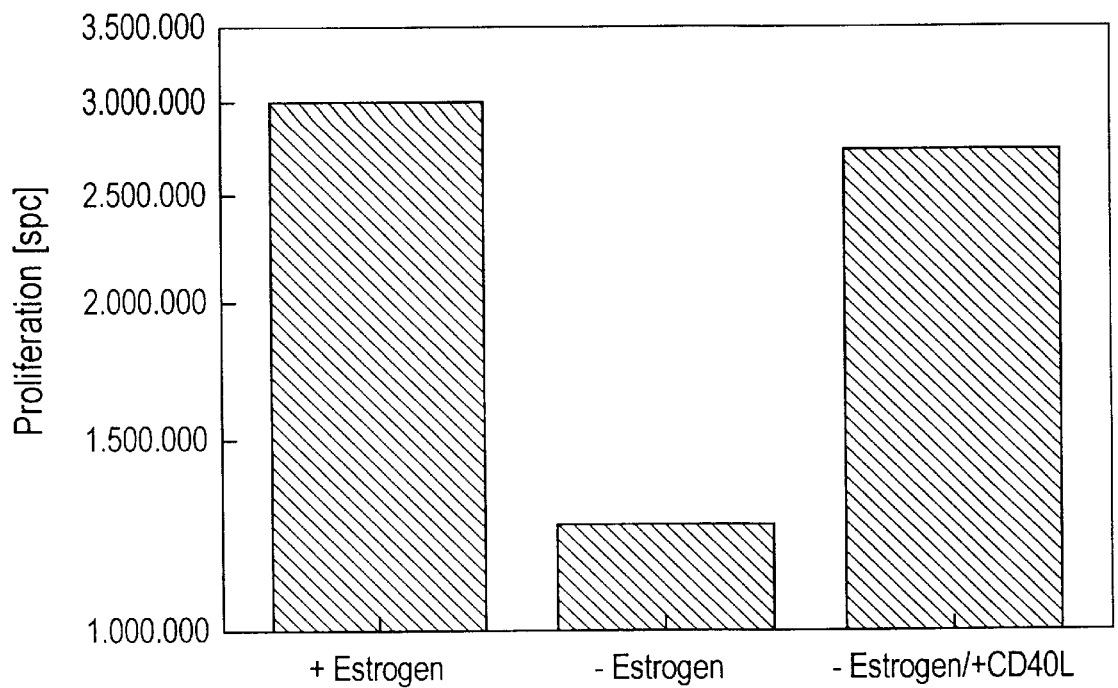
FIG. 3 shows that co-cultivation with CD40L-expressing feeder cells preserves the allostimulatory properties of EREB2–5 cells also in the absence of estrogen.
Figure 5:
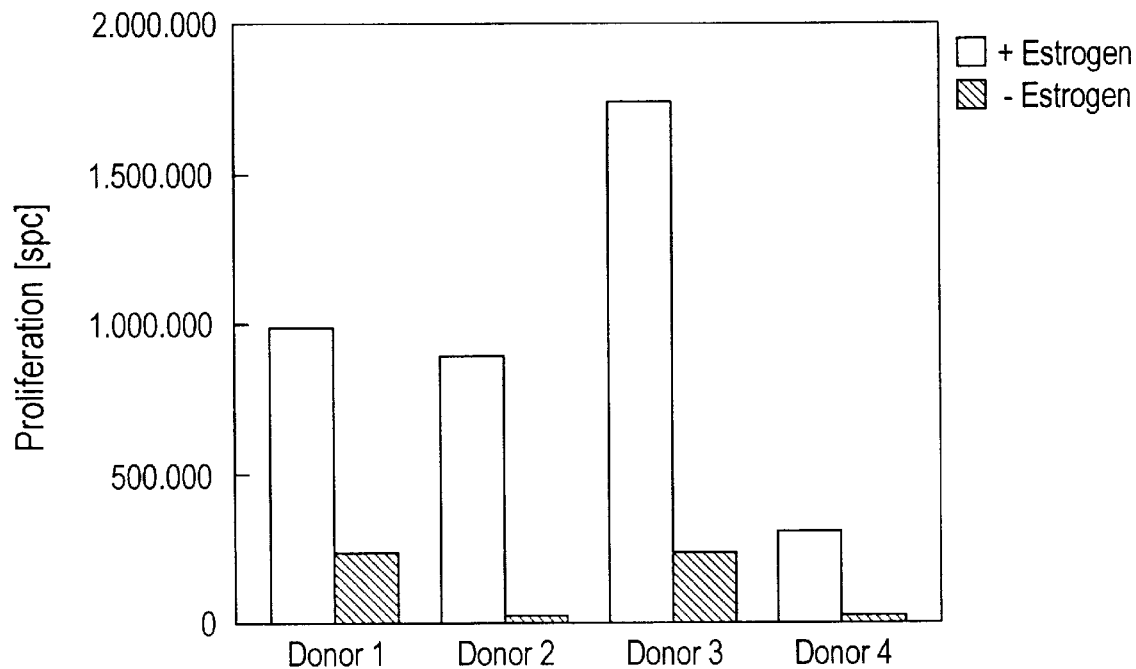
FIG. 5 shows that the allostimulatory capacity of EREB2–5 cells depends on the presence of functional EBNA2.

By co-cultivation of EREB2–5 cells with the PBMCs of allogenic donors the T cells included in these PBMCs were stimulated and started to proliferate (FIG. 5). After switching off the EBNA2 function the proliferation was observed to be clearly reduced. To restore the immunostimulatory competence of the EREB2–5 cells, the cells were cultured for 4 days after switching off the EBNA2 function on a CD40 ligand-expressing fibroblast feeder layer and then used as APCs. By this treatment, the stimulatory competence could be restored (FIG. 3). The observation that in the presence of EBNA2 function EREB2–5 cells have a good stimulatory competence for PBMCs (FIG. 5) and cloned T cells (FIG. 5), but in the absence of EBNA2 function may serve as APCs only for already primed T cells (FIG. 4) leads to the conclusion that the method of the invention according to claim 2 may be practiced as an alternative embodiment. The individual steps of this claim 2 are already outlined above.

Purification of the T cells may be for example performed by FACS.

In the following, the experiments described above which have led to the methods according to the invention will be described in detail.

B cells were used as the antigen-presenting cells. Among the EBV genes introduced into the antigen-presenting cells required for immortalization, the EBNA2 gene was rendered controllable by means of an estrogen binding domain. This only refers to one possible embodiment of the methods according to the invention. As detailed above, also other embodiments are possible being well within the skill of a scientist working in the field of immunology.

1. Use of conditionally EBV-immortalized LCLs for T cell activation following switching off EBNA2 and CD40 stimulation In this embodiment of the method according to the invention conditionally immortalized LCLs are generated on a LCL donor and employed as antigen-presenting cells. The desired antigen is expressed in these LCLs.

The procedures used in obtaining the data shown in FIGS. 1, 2, and 3 were as follows.

For FIG. 1: EREB2–5 cells and A1 cells ($5 \times 10^4$/well of each) were cultured for 4 days in the presence or absence of 1 $\mu$M estradiol (Merck, Darmstadt) in 96-well microtiter plates in a volume of 200 $\mu$L/well. $^3$H-thymidine (Amersham, Braunschweig, 5.6 kBq) was added, and after a further 24 hours the incorporation of radiolabeled thymidine into the DNA was determined using a liquid scintillation counter (LKB, Freiburg).

For FIG. 2: EREB2–5 cells ($2.5 \times 10^6$) were cultured for 4 days in the presence or absence of 1 $\mu$M estradiol in 6-well plates in a volume of 5 $\mu$L/well, labeled with $^{51}$Cr and used as target cells for the LMP2-specific CTL clone YKc14 (a kind gift of A. Rickinson, Birmingham, UK). For this purpose, the target cells were incubated together with the CTLs in a ratio of effector to target cells of 5:1 in 96-well round-bottom plates in a volume of 200 $\mu$L/well. After 4 hours, 100 $\mu$L of supernatant were removed from each well and the radioactivity released was detected using a gamma counter (Cobra Auto-Gamma, LKB).

For FIG. 3: EREB2–5 cells ($2.5 \times 10^6$) were cultured for 4 days in the presence or absence of 1 $\mu$M estradiol as well as in the presence of estradiol and in the presence of CD40L-expressing feeder cells ($10^6$) in cell culture flasks in a volume of 10 mL medium. The cells were treated with mitomycin C (Boehringer Mannheim) (50 $\mu$g/mL, 45 min), washed three times with phosphate buffer (PBS) and employed as stimulator cells ($10^4$/well each) for PBMCs (each $2 \times 10^4$/well) of a healthy donor (donor MS, HLA halotype: A3, 24; B7, 56; Cw1, 7; DR2, 4; EBV-positive). For this purpose, the stimulator cells and the PBMCs were incubated for 6 days in 96-well microtiter plates. PBMC proliferation was determined using a test kit of Boehringer company ("Cell Proliferation ELISA").

The culture medium used for all of FIGS. 1–3 was: RPMI1640 (Gibco, Karlsruhe)+10% fetal calf serum (Gibco), penicillin/streptomycin (Gibco; $10^5$ I.U./$10^5$ $\mu$g/L and amphotericin B (Gibco; 750 $\mu$g/mL).

The LCLs thus obtained are then expanded in the presence of estrogen. After estrogen depletion these LCLs will cease to proliferate (FIG. 1) and simultaneously loose their ability to stimulate CTLs having a specificity for EBNA2-controlled EBV-encoded antigens (FIG. 2). However, since the desired antigen is expressed from a promotor still active after estrogen depletion and the immunostimulatory capacity of these cells is preserved after co-cultivation with CD40L-expressing feeder cells (FIG. 3) this embodiment of the method according to the invention provides cultivation of the LCLs after estrogen depletion in the presence of such feeder cells or another CD40 stimulus (soluble ligand, antibody). After several days PBMCs of the patient are then added and the activated T cells cultured according to the usual standard procedures.

Our method has been optimized for the generation of class I-restricted CTLs. However, the methods already known for the introduction of endogenous antigens into the class II pathway of antigen processing (fusion of the antigen to so-called CLIP peptides, secretion of the antigen) allow for the use of the same conditional LCLs in the generation of CD4-positive T helper cells ($T_h$).

The method described above has been optimized for the generation of CTLs because expression of the desired antigen is to be performed primarily endogenously so that the class I pathway of antigen processing is addressed. To induce T helper cells the antigen must be introduced into the class II pathway (also referred to as exogenous pathway). This may be carried out using methods already known by a) fusion of the antigen to signal peptides enabling the secretion of the antigen so that the antigen is able to leave the cell and from there enter the exogenous processing pathway; b) fusion of the antigen with peptides (so-called CLIP) derived from the class II-associated invariant chain (Ii) usually directing newly synthesized class II molecules into a compartment in which they are associated with antigenic peptides; this results in the antigen taking the same way inside the cells as usually do empty class II molecules; c) addition of the antigen from the outside. However, for this method it is required that the antigen or antigenic peptides can be synthesized or isolated from natural products in almost pure form.

2. Use of conditionally EBV-immortalized LCLs in the reactivation of a pre-existing T cell activation after switching off EBNA2

This modification of the method described above may be used in the case of pre-activated T cells already present in a patient. This is rendered obvious for numerous diseases since antigen-specific T cells may be established from such patients in vitro with high frequency. For this purpose conditional LCLs of the patient are established as in 1. Subsequently these cells are depleted for estrogen and these cells are incubated with the PBMCs of the patient. These conditions enable an activation of previously primed antigen-specific CTLs (FIG. 4). The resulting CTLs may then be expanded using standard procedures.

The procedure used in obtaining the data shown in FIG. 4 was as follows. EREB2–5 cells ($2.5\times10^6$) were cultured for 4 days (using the culture medium used for the preceding Figures) in the presence or absence of 1 $\mu$M estradiol in a volume of 5 $\mu$L/well, infected with vaccinia viruses containing the EBNA3 gene in recombinant form at a moi of 10 (a kind gift of A. Rickinson, Birmingham, UK), labeled with $^{51}$Cr after overnight culture at 37° C., and employed as target cells for the EBNA3-specific CTL clone CMc50 (a kind gift of A. Rickinson, Birmingham, UK). For this purpose, the target cells were incubated together with the CTLs in a ratio of effector to target cells of 5:1 in 96-well round bottom plates in a volume of 200 $\mu$L/well. After 4 hours, 100 $\mu$L of supernatant were removed from each well and the radioactivity released was detected using a gamma counter (Cobra Auto-Gamma, LKB).

This method described above may also be used as an embodiment of the method described in 1 since a regular re-stimulation of the cells i.a. is desirable for the expansion of the T cells. For re-stimulation of the cells there may always be used the method described in 2. It has the advantage that it does not require CD40L.

3. Use of conditionally EBV-immortalized LCLs in T cell activation after switching off EBNA2 in a two-step process Starting from the same conditionally immortalized LCLs this embodiment of the method according to the invention provides the incubation of these cells in a first step in the presence of estrogen with the PBMC of the patient thereby activating not only the desired antigen-specific T cells but also EBV-specific T cells. Subsequently for re-stimulation the LCLs are cultured in the absence of estrogen thereby restimulating the antigen-specific T cells (FIG. 4) but not the EBV-specific T cells (FIG. 2).

4. Use of allogenic conditionally EBV-immortalized LCLs in T cell activation after switching off EBNA2

(a) One-step process

This embodiment differs in an essential step from the embodiments 1–3:

In a preparative stage, conditionally immortalized LCLs from donors are prepared which express the desired antigen. After EBNA2 is switched off these LCLs are employed as APCs for the PBMCs of a donor syngenic for a corresponding MHC molecule with the donor of the LCLs. This means that for example the PBMCs of a HLA A2-positive donor are incubated with the LCLs of an equally A2-positive donor thereby expanding only the A2-restricted T cells already primed in vivo having the desired specificity. EBV-specific T cells fail to be activated for the reasons already mentioned. The important point in this case is that under these conditions allospecific T cells also fail to be activated (FIG. 5). Thus, an activation of antigen-specific T cells by allogenic LCLs is possible. If used in therapy this method is of particular importance because no LCLs have to be established of the patient individually so that valuable time is saved for therapy.

The procedure used in obtaining the data shown in FIG. 5 was as follows. EREB2–5 cells ($2.5\times10^6$) were cultured for 4 days in the presence or absence of 1 $\mu$M estradiol in a volume of 5 $\mu$L/well. The culture medium was the same as that used for the preceding Figures. The cells were treated with mitomycin C (50 $\mu$g/mL, 45 min), washed three times with phosphate buffer (PBS) and employed as stimulator cells ($10^4$/well each) for PBMCs (each $2\times10^4$/well) of various healthy donors. For this purpose, the stimulator cells and the PBMCs were incubated for 6 days in 96-well microtiter plates. Proliferation of the PBMCs was determined using a test kit of Boehringer company ("Cell Proliferation ELISA").

(b) Two-step-process

Figure 6:
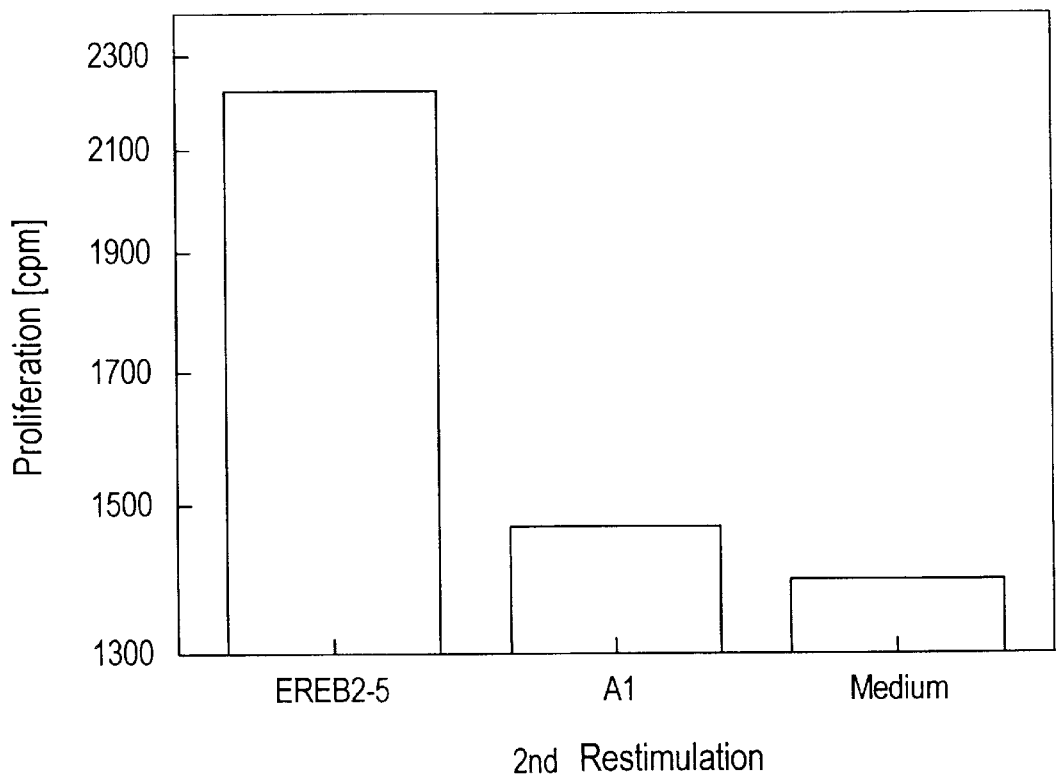
FIG. 6 shows that primary stimulation of allogenic PBMC by EREB2–5 cells fails to lead to the induction of an immune response against A1 cells.

This method also uses allogenic conditionally immortalized LCLs. Since the method described in 4a is only useful in the activation of primed T cells this modification of the method provides in a first step to perform an activation of the allogenic T cells with LCLs in the presence of EBNA2 function with subsequent re-stimulation of the cells in the absence of estrogen. The fundamental mechanisms have been outlined already in point 3. It is important that besides EBV-specific T cell activation also the allostimulation by LCLs is reduced after EBNA2 has been switched off. T cells stimulated with EREB2–5 cells as the alloantigen show no proliferation after re-stimulation with A1 showing that the lack of allostimulation by LCLs in the absence of EBNA2 function may not be overcome by priming the T cells in the presence of EBNA2 function (FIG. 6).

If contrary to expectation under these conditions a measurable allostimulation occurs it would be most suitable to use conditionally immortalized LCLs for re-stimulation expressing the same desired antigen but being derived from a third person and expressing other HLA alleles (exept the HLA molecules also present in the patient to immunize and required for antigen presentation) than those of the LCLs used in primary stimulation. Thus, the allospecific T cells activated during primary stimulation should not be activated during secondary stimulation since the LCLs used lack the relevant alloantigens.

The possibilities to employ T cell lines and clones established by any of the methods of the invention are on the one hand in immunological basic research and on the other hand also and precisely in the adaptive transfer of such cells into patients for therapeutic modulation of the course of the disease.

The T cells induced by the in vitro method of the invention may optionally be purified and isolated. Afterwards, they would be adoptively transferred to patients for therapeutic use, for example in tumor therapy or control of viral infections such as the feared cytomegalovirus infection following bone-marrow transplantations.

Thus, according to the invention conditionally immortalized antigen-presenting cells are employed in the stimulation of immunocompetent T cells. Surprisingly, it has been discovered according to the invention that after switching off the immortalizing function for example by switching off the EBNA2 protein also the immunostimulatory property of the antigen-presenting cells for unprimed T cells, i.e. T cells not previously stimulated for the desired antigen, almost completely ceases. Moreover, it has been surprisingly found that by stimulation via the interaction of CD40 with its ligand the immunological recognizability of antigen-presenting cells for unprimed T cells may be restored.

General information with respect to methodology

The $^3$H incorporation assay and the $^{51}$Cr release test were performed according to standard procedures such as those outlined in [14, 15]. The "Cell proliferation ELISA" of Boehringer company was carried out according to the manufacturer's instructions. The infection of cells with recombinant vaccinia viruses was effected at a moi (multiplicity of infection) of 10:1. For this purpose the target cells (500,000) were centrifuged in 10 ml tubes and the pellet was incubated with supernatant containing virus for 1.25 h with mixing from time to time. Then, 2 ml of culture medium were added and the tube was stored overnight in an incubator and subsequently treated as usual for target cells of the $^{51}$Cr release assay.

In the following a possible therapeutic use of the present invention is described.

A patient is suffering from chronic myeloid leukemia with expression of the Bcr-Abl fusion protein. According to our knowledge this fusion protein is not only the agent responsible for leukemia development but also a tumor-specific antigen since the amino acid sequence generated by fusion is only expressed in tumor cells. The existence of T cells specifically recognizing the site of fusion has been already described. Peripheral blood mononucleated cells have been obtained from the patient and the donor prior to bone marrow transplantation and the B lymphocytes have been conditionally immortalized by EBV. Starting from these cells additional cell lines are prepared which were transfected with Bcr-Abl and express the Bcr-Abl fusion protein. Following hormone depletion, the conditionally immortalized cells expressing Bcr-Abl of the patient are used as antigen-presenting cells in the stimulation of the T cells derived from the donor.The specificity of the T cells obtained is examined by means of the conditionally immortalized normal as well as Bcr-Abl-expressing cells of the patient and the donor. T cells recognizing the Bcr-Abl fusion protein in combination with HLA molecules of the recipient are expanded in vitro and re-infused into the patient in the case of a recurrency or a blast crisis. By the T cells having a defined specificity the tumor cells are killed and the patient is healed.

References

[1] Immunological principles may be found in the respective textbooks. If not otherwise indicated important informations may be found for example in Janeway, C. A., Jr. & P. Travers (1994) Immunobiology. Oxford: Blackwell Scientific Publications. Particularly Chapters 4 und 7.

[2] Staerz, U. D., H. Karasuyama & A. M. Garner (1987). Cytotoxic T lymphocytes against a soluble protein. Nature 329:449.

[3] Carbone, F. R. & M. J. Bevan (1989). Induction of ovalbumin-specific cytotoxic T cells by in-vivo peptide immunisation. J. Exp. Med. 169:603.

[4] Carbone, F. R., M. W. Moore, J. M. Sheil & M. J. Bevan (1988). Induction of cytotoxic T lymphocyts by primary in vitro stimulation with peptides. J. Exp. Med. 167:1767.

[5] Young, J. W. & K. Inaba (1996). Dendritic cells as adjuvants for class I major histocompatibility complex-restricted antitumor immunity. J. Exp. Med. 183:7.

[6] Aichele, P. K., K. Brduscha-Riem, R. M. Zinkernagel, H. Hengartner & H. Pircher (1995). T cell priming versus T cell tolerance induced by synthetic peptides. J. Exp. Med. 182:261.

[7] Klein, G. (1994). Epstein-Barr virus strategy in normal and neoplastic B cells. Cell 77:791.

[8] Pecher, G. & O. J. Finn (1997). Induction of cellular immunity in chimpanzees to human tumor-associated antigen mucin by vaccination with MUC-1 cDNA transfected Epstein-Barr virus-immortalized autologous B cells. Proc. Natl. Acad. Sci. USA 93:1699.

[9] Guilhot, S., P. Fowler, G. Portillo, R. F. Margolskee, C. Ferrari, A. Bertoletti & F. V. Chisari (1992). Hepatitis B Virus (HBV)-specific cytotoxic T-cell response in humans: production of target cells by stable expression of HBV-encoded proteins in immortalized human B-cell line. J. Virol. 66:2670.

[10] Penna, A., P. Fowler, A. Bertoletti, S. Guilhot, B. Moss, R. F. Margolskee, A. Cavalli, A. Valli, F. Fiaccadori, F. V. Chisari & C. Ferrari (1992). Hepatitis B virus (HBV)-specific cytotoxic T-cell (CTL) response in humans: characterization of HLA class II-restricted CTLs that recognize endogenously synthesized HBV envelope antigens. J. Virol. 66:1193.

[11] Kempkes, B., D. Spitkovsky, P. Jansen-Dürr, J. W. Ellwart, E. Kremmer, H.-J. Delecluse, C. Rottenberger, G. W. Bornkamm & W. Hammerschmidt (1995). B-cell proliferation and induction of early G1-regulating proteins by Epstein-Barr virus mutants conditional for EBNA2. EMBO J. 14:88.

[12] Polack, A., K. Hörtnagel, A. Pajic, B. Christoph, B. Baier, M. Falk, J. Mautner, C. Geltinger, G. W. Bornkamm & B. Kempkes (1996). c-myc activation renders proliferation of Epstein-Barr virus (EBV)-transformed cells independent of EBV nuclear antigen 2 and latent membrane protein 1. Proc. Natl. Acad. Sci. USA 93:10411.

[13] Zimber-Strobl, U., B. Kempkes, G. Marschall, R. Zeidler, C. Van Kooten, J. Banchereau, G. W. Bornkamm and W. Hammerschmidt (1996). Epstein-Barr virus latent membrane protein (LMP1) is not sufficient to maintain proliferation of B cells but both it and activated CD40 can prolong their survival. EMBO J. 15:7070.

[14] Staege, M. S., T. Dick, R. Ertl, U. Jahnel, H. Nawrath, H.-G. Rammensee and A. B. Reske-Kunz (1994). The antigen-self-presentation function of the cytotoxic T cell clone 10BK.1 depends on reciprocal peptide presentation. Immunology 81:333.

[15] Staege, M. S., T. Dick and A. B. Reske-Kunz. (1996). Functionally active T cell receptor/CD3 complexes are present at the surface of cloned cytotoxic T cells without fluorescence-immunological detectability. Cell. Immunol. 171:62.

What is claimed is:

1. A method for the stimulation of T cells having a desired antigen specificity, said method comprising:

(a) introducing immortalizing genes into antigen-presenting cells in a manner that permits the regulation of the expression of at least one of these genes and/or the function of the product of that gene to achieve conditionally immortalized antigen-presenting cells;
- (b) introducing a gene encoding the desired antigen into the conditionally immortalized cells obtained in step (a) in a manner that permits the expression of the antigen after stopping the expression and/or abolishing the function of at least one of the immortalizing genes or gene products;
- (c) expanding the conditionally immortalized antigen-presenting cells by expression of the immortalizing genes and/or by functional activation of the immortalizing gene product;
- (d) completing the proliferation of the immortalized antigen-presenting cells by stopping the expression and/or abolishing the function of at least one of the controllable immortalizing genes or gene products;
- (e) continuing the expression of the antigen; and
- (f) adding leukocytic cells including at least T cells and cultivating the cell mixture to stimulate the T cells directed against the desired antigen.

2. A method in accordance with claim 1, further comprising purifying and isolating the T cells stimulated by step (f).

3. A method in accordance with claim 1, in which the added antigen-presenting cells are obtained from a first donor and in step (f) the allogenic leukocytic cells employed are obtained from a second donor who is syngenic for at least one corresponding MHC molecule serving for antigen presentation with the first donor.

4. A method in accordance with claim 1, in which the antigen-presenting cells of step (a) and the leukocytic cells of step (f) are obtained from a common donor.

5. A method for the stimulation of T cells having a desired antigen specificity, said method comprising:
- (a) introducing immortalizing genes into antigen-presenting cells in a manner that permits the regulation of the expression of at least one of these genes and/or the function of that gene product to achieve conditionally immortalized antigen-presenting cells;
- (b) introducing a gene encoding the desired antigen into the conditionally immortalized cells obtained in step (a) in a manner that permits expression of the antigen after stopping the expression and/or abolishing the function of at least one of the immortalizing genes or gene products;
- (c) expanding the conditionally immortalized antigen-presenting cells by expression of the immortalizing genes and/or by functional activation of the immortalizing gene product;
- (d) adding leukocytic cells including at least T cells to a first portion of the immortalized cells obtained in steps (a) through (c) expressing the desired antigen and culturing the cell mixture to stimulate the T cells directed against the desired antigen;
- (e) completing the proliferation of a second portion of the immortalized cells obtained in steps (a) through (c) by stopping the expression and/or abolishing the function of at least one of the controllable immortalizing genes or gene products required for immortalization; and
- (f) co-cultivating the antigen-presenting cells after stopping the expression and/or abolishing the function of at least one of the controllable immortalizing genes or gene products of (e) with the T cells stimulated in step (d) for restimulation of the T cells directed against the desired antigen.

6. A method in accordance with claim 5, further comprising purifying and isolating the T cells stimulated by step (f).

7. A method in accordance with claim 5, in which the added antigen-presenting cells are obtained from a first donor and in step (d) the allogenic leukocytic cells employed are obtained from a second donor who is syngenic for at least one corresponding MHC molecule serving for antigen presentation with the first donor.

8. A method in accordance with claim 5, in which the antigen-presenting cells of step (a) and the leukocytic cells of step (d) are obtained from a common donor.

9. A method in accordance with claims 1 or 5, in which said immortalizing genes are genes selected from the group consisting of Epstein-Barr virus genes, adenoviral genes, and oncogenes.

10. A method in accordance with claims 1 or 5, in which the vectors for the introduction of the gene encoding the desired antigen into the immortalized antigen-presenting cells are vectors obtained from a virus selected from the group consisting of Epstein-Barr virus, adenoviruses, retroviruses, foamyviruses, poxviruses, and SV40 virus.

11. A method in accordance with claims 1 or 5, in which the immortalizing genes are a member selected from the group consisting of the EBNA2 gene, the EBNA3a gene, the EBNA3b gene, the EBNA3c gene, and the LMP gene of Epstein-Barr virus.

12. A method in accordance with claims 1 or 5, in which the immortalizing genes are genes that may be regulated by hormones or antibiotics.

13. A method in accordance with claims 1 or 5, in which steps (a) and (b) are performed simultaneously.

14. A method in accordance with claims 1 or 5, in which the gene coding the desired antigen is arranged on the same vector that bears the immortalizing genes and in which at least one of the immortalizing genes is controllable.

15. A method in accordance with claims 1 or 5, further comprising, prior to the step of adding leukocytic cells, modulating the immunostimulatory properties of the immortalized cells expressing the desired antigen by culturing said immortalized cells in the presence of a member selected from the group consisting of a CD40 stimulus and cytokines.

16. A method in accordance with claims 1 or 5, in which the antigen-presenting cells are a member selected from the group consisting of B cells, macrophages, dendritic cells, and fibroblasts.

17. A method in accordance with claims 1 or 5, further comprising, prior to the step of adding leukocytic cells, permanently suppressing the growth of the immortalized antigen-presenting cells.

18. A method in accordance with claims 1 or 5, in which said T cells are obtained from mammals.

19. A method in accordance with claims 1 or 5, in which said T cells are obtained from a member selected from the group consisting of humans and rodents.

20. A method for the stimulation of T cells having a desired antigen specificity, said method comprising:
- (a) introducing immortalizing genes into antigen-presenting cells in a manner that permits regulation of the expression of at least one of these genes and/or the function of that gene product to achieve conditionally immortalized antigen-presenting cells;
- (b) expanding the conditionally immortalized antigen-presenting cells by expression of the immortalizing genes and/or by functional activation of the immortalizing gene product;
- (c) completing the proliferation of the immortalized antigen-presenting cells by stopping the expression and/or abolishing the function of at least one of the controllable immortalizing genes or gene products;

(d) introducing a gene encoding the desired antigen into the immortalized cells obtained in step (c) in a manner that permits the expression of the antigen after stopping the expression and/or abolishing the function of at least one of the immortalizing genes or gene products, (e) immediately after step (d), continuing the expression of the antigen;

(f) adding leukocytic cells including at least T cells and cultivating the cell mixture to stimulate the T cells directed against the desired antigen; and (g) optionally purifying and isolating the stimulated T cells.

21. A method for the stimulation of T cells having a desired antigen specificity, said method comprising:

(a) introducing immortalizing genes into antigen-presenting cells in a manner that permits regulation of the expression of at least one of these genes and/or the function of that gene product to achieve conditionally immortalized antigen-presenting cells;

(b) expanding the conditionally immortalized antigen-presenting cells by expression of the immortalizing genes and/or by functional activation of the immortalizing gene product;

(c) introducing a gene encoding the desired antigen into the immortalized cells obtained in step (b) in a manner that permits expression of the antigen after stopping the expression and/or abolishing the function of at least one of the immortalizing genes or gene products, (d) immediately after step (c), adding leukocytic cells including at least T cells to a first portion of the immortalized cells obtained in steps (a) through (c) expressing the desired antigen and culturing the cell mixture to stimulate the T cells directed against the desired antigen;

(e) completing the proliferation of a second portion of the immortalized cells obtained in steps (a) through (c) by stopping the expression and/or abolishing the function of at least one of the controllable immortalizing genes or gene products required for immortalization;

(f) co-cultivating the antigen-presenting cells after stopping the expression and/or abolishing the function of at least one of the controllable immortalizing genes or gene products of (e) with the T cells stimulated in step (d) for restimulation of the T cells directed against the desired antigen; and (g) optionally purifying and isolating the stimulated T cells.

22. A method for the stimulation of T cells having a desired antigen specificity, said method comprising:

(a) introducing immortalizing genes into antigen-presenting cells in a manner that permits regulation of the expression of at least one of these genes and/or the function of that gene product to achieve conditionally immortalized antigen-presenting cells;

(b) expanding the conditionally immortalized antigen-presenting cells by expression of the immortalizing genes and/or by functional activation of the immortalizing gene product;

(c) introducing a gene encoding the desired antigen into a first portion of the immortalized cells obtained in step (b) in a manner that permits expression of the antigen after stopping the expression and/or abolishing the function of at least one of the immortalizing genes or gene products;

(d) immediately after step (c), adding leukocytic cells including at least T cells to said portion of the immortalized cells obtained in steps (a) through (c) expressing the desired antigen and culturing the cell mixture to stimulate the T cells directed against the desired antigen, (e) introducing a gene encoding the desired antigen into a second portion of the immortalized cells obtained in step (b) in a manner that permits expression of the antigen after stopping the expression and/or abolishing the function of at least one of the immortalizing genes or gene products;

(f) completing the proliferation of said second portion of the immortalized cells obtained in step (e) by stopping the expression and/or abolishing the function of at least one of the controllable immortalizing genes or gene products required for immortalization;

(g) immediately after step (f), co-cultivating the antigen-presenting cells after stopping the expression and/or abolishing the function of at least one of the controllable immortalizing genes or gene products of (f) with the T cells stimulated in step (d) for re-stimulation of the T cells directed against the desired antigen; and (h) optionally purifying and isolating the stimulated T cells.

* * * * *